(12) United States Patent
Liao et al.

(10) Patent No.: US 12,258,453 B2
(45) Date of Patent: Mar. 25, 2025

(54) METHOD FOR IMPROVING HUE OF RECYCLED BIS-2-HYDROXYLETHYL TEREPHTHALATE BY USING IONIC LIQUIDS

(71) Applicant: NAN YA PLASTICS CORPORATION, Taipei (TW)

(72) Inventors: Te-Chao Liao, Taipei (TW); Jung-Jen Chuang, Taipei (TW); Wei-Sheng Cheng, Taipei (TW); Zhang-Jian Huang, Taipei (TW); Yu-Ti Tseng, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 371 days.

(21) Appl. No.: 17/808,893

(22) Filed: Jun. 24, 2022

(65) Prior Publication Data

US 2023/0060362 A1    Mar. 2, 2023

(30) Foreign Application Priority Data

Aug. 26, 2021 (TW) ................................ 110131575

(51) Int. Cl.
| | | |
|---|---|---|
| *C08J 11/24* | (2006.01) | |
| *B01D 9/00* | (2006.01) | |
| *B01D 15/12* | (2006.01) | |
| *B01D 15/16* | (2006.01) | |
| *C07C 67/56* | (2006.01) | |
| *C08J 11/28* | (2006.01) | |

(52) U.S. Cl.
CPC ............. *C08J 11/24* (2013.01); *B01D 9/0013* (2013.01); *B01D 15/12* (2013.01); *B01D 15/161* (2013.01); *C07C 67/56* (2013.01); *C08J 11/28* (2013.01); *B01D 2009/0086* (2013.01); *C08J 2367/02* (2013.01); *Y02W 30/62* (2015.05)

(58) Field of Classification Search
None
See application file for complete search history.

(56) References Cited

U.S. PATENT DOCUMENTS

| 9,255,194 B2 | 2/2016 | Allen et al. |
|---|---|---|
| 2012/0231346 A1 | 9/2012 | Tsujii et al. |
| 2015/0105532 A1 | 4/2015 | Allen et al. |
| 2015/0231529 A1 | 8/2015 | Akolekar et al. |

(Continued)

FOREIGN PATENT DOCUMENTS

| CN | 100344604 C | 10/2007 |
|---|---|---|
| CN | 107406618 A | 11/2017 |
| CN | 110291146 A | 9/2019 |

(Continued)

*Primary Examiner* — Katie L. Hammer
(74) *Attorney, Agent, or Firm* — Li & Cai Intellectual Property (USA) Office

(57) ABSTRACT

A method for improving hue of recycled bis-2-hydroxylethyl terephthalate by using ionic liquids including providing a recycled polyester fabric; using a chemical de-polymerization liquid to chemically de-polymerize the recycled polyester fabric to form a de-polymerization product; mixing the de-polymerization product with water to form an aqueous phase liquid; dispersing an ionic liquid impurity adsorption material into the aqueous phase liquid to adsorb impurities originally present in the recycled polyester fabric.

9 Claims, 1 Drawing Sheet

(56) References Cited

U.S. PATENT DOCUMENTS

2020/0024420 A1    1/2020  Castillo et al.

FOREIGN PATENT DOCUMENTS

| JP | 200053802 A | 2/2000 | | |
|----|-------------|--------|---|---|
| JP | 2008088096 A | 4/2008 | | |
| JP | 2015535738 A | 12/2015 | | |
| JP | 2016536291 A | 11/2016 | | |
| JP | 2018502977 A | 2/2018 | | |
| JP | 2020507644 A | 3/2020 | | |
| WO | WO 2011049113 A1 | 4/2011 | | |
| WO | WO-2017198786 A1 * | 11/2017 | ............. | C08J 11/10 |
| WO | WO-2018143798 A1 * | 8/2018 | ............ | B01J 23/745 |

* cited by examiner

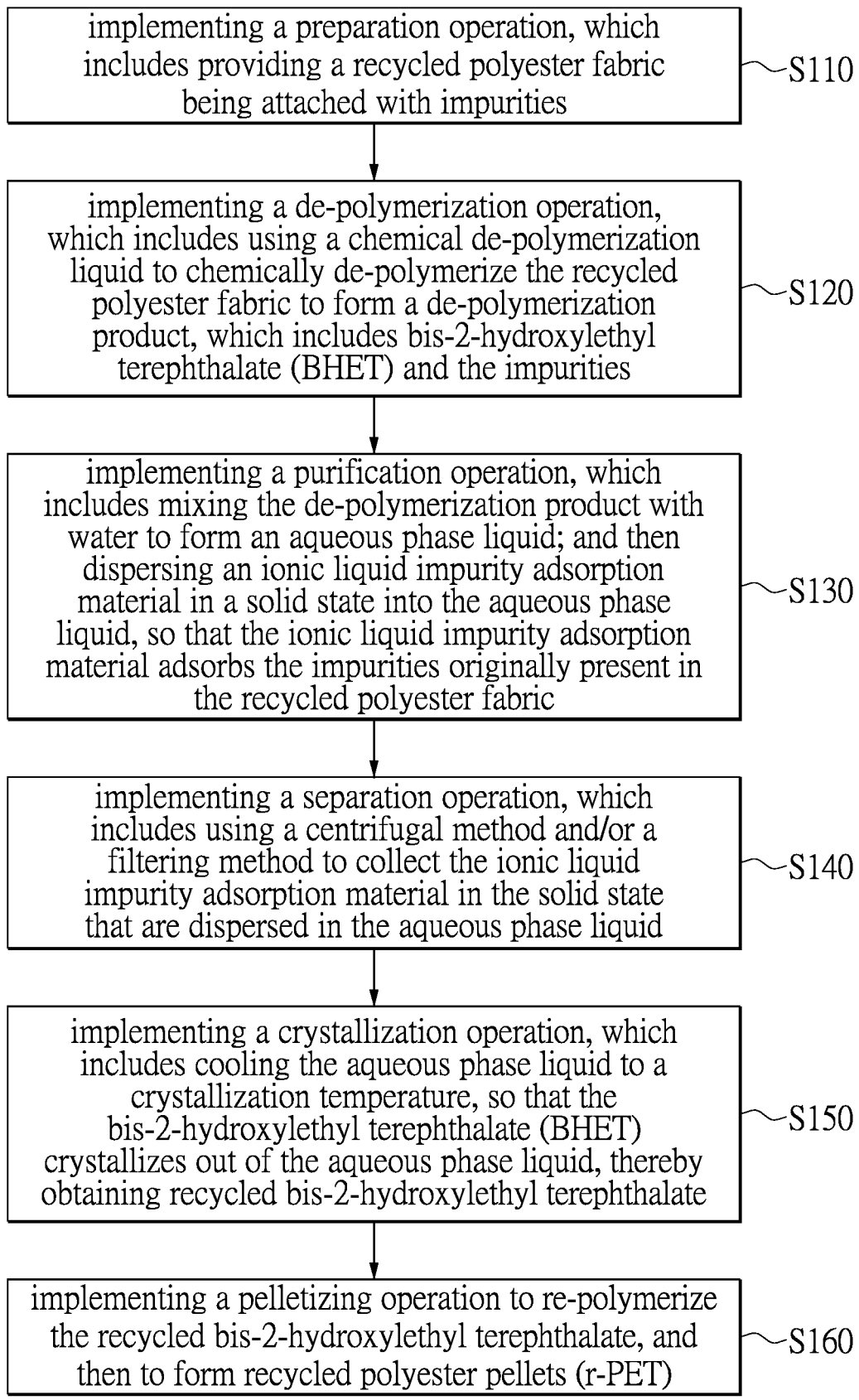

METHOD FOR IMPROVING HUE OF RECYCLED BIS-2-HYDROXYLETHYL TEREPHTHALATE BY USING IONIC LIQUIDS

CROSS-REFERENCE TO RELATED PATENT APPLICATION

This application claims the benefit of priority to Taiwan Patent Application No. 110131575, filed on Aug. 26, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for recycling a polyester material, and more particularly to a method for improving hue of recycled bis-2-hydroxylethyl terephthalate by using ionic liquids.

BACKGROUND OF THE DISCLOSURE

In the related art, a conventional chemical recycling method of polyester fabrics (PET fabric) essentially adopts chemical de-polymerization of the polyester fabrics with a chemical de-polymerization liquid, such as glycol, so as to form a de-polymerization product. The de-polymerization product mainly includes bis(2-hydroxyethyl) terephthalate (BHET). However, the conventional chemical recycling method requires a complicated purification process to remove dyes and other impurities originally present in the polyester fabrics before the BHET can be re-polymerized to form high-quality recycled polyester pellets (r-PET).

In the above-mentioned purification process of BHET, a conventional purification technology is to use an activated carbon material or an ion exchange resin to adsorb impurities such as dyes on the crude BHET product containing ethylene glycol (EG). Alternatively, the BHET can be separated by distillation. However, both of the above two purification methods have disadvantages such as poor recovery quality of BHET (i.e., poor heat resistance) and high recovery costs.

U.S. Pat. No. 9,255,194 (B2) proposes a method for de-polymerization of polyester fabrics. Although the method proposed in this patent can remove impurities such as dyes and recycle the catalyst, said method still requires complicated purification procedures for the purification of BHET, while the recovery rate of BHET is low and the recovery quality of BHET is poor.

Patent No. CN 100344604 (C) proposes a method for de-polymerization of polyester fabrics. The method proposed in this patent also requires a complicated purification procedure in the purification of BHET, which results in high material recovery costs and poor recovery quality of BHET.

SUMMARY OF THE DISCLOSURE

In response to the above-referenced technical inadequacies, the present disclosure provides a method for improving hue of recycled bis-2-hydroxylethyl terephthalate by using ionic liquids.

In one aspect, the present disclosure provides a method for improving hue of recycled bis-2-hydroxylethyl terephthalate by using ionic liquids, which includes implementing a preparation operation, which includes providing a recycled polyester fabric, and the recycled polyester fabric being attached with impurities; implementing a de-polymerization operation, which includes using a chemical de-polymerization liquid to chemically de-polymerize the recycled polyester fabric to form a de-polymerization product, which includes the bis-2-hydroxylethyl terephthalate (BHET) and the impurities; implementing a purification operation, which includes mixing the de-polymerization product with water to form an aqueous phase liquid; and then dispersing an ionic liquid impurity adsorption material in a solid state into the aqueous phase liquid, so that the ionic liquid impurity adsorption material adsorbs the impurities originally present in the recycled polyester fabric; and implementing a separation operation, which includes using a centrifugal method and/or a filtering method to collect the ionic liquid impurity adsorption material in the solid state that are dispersed in the aqueous phase liquid.

In certain embodiments, in the de-polymerization operation, the chemical de-polymerization liquid is ethylene glycol (EG), and the chemical de-polymerization liquid is heated to a de-polymerization temperature between 180° C. and 260° C. to chemically de-polymerize the recycled polyester fabric.

In certain embodiments, in the purification operation, the ionic liquid impurity adsorption material includes a substrate and the ionic liquids that are grafted onto the substrate.

In certain embodiments, the substrate is a granular material and has an average particle size of between 0.8 micrometers and 800 micrometers.

In certain embodiments, in the ionic liquid impurity adsorption material, a grafted quantity of the ionic liquids grafted onto per gram of the substrate is between $10^6$ and $10^{20}$.

In certain embodiments, in the ionic liquid impurity adsorption material, the ionic liquids are at least one material selected from a group consisting of 1-butyl-3-methylimidazolium hexafluorophosphate (BMI-PF6), 1-butyl-3-methylimidazolium tetrachlorozincate ($BMI_2ZnCl_4$), 1-butyl-3-methylimidazolium tetrachloroironate ($BMI_2FeCl_4$), 1-butyl-3-methylimidazolium tetrachloroironate ($BMI_2CoCl_4$), and 1-butyl-3-methylimidazolium tetrachlorocobaltate ($BMI-BF_4$).

In certain embodiments, in the ionic liquid impurity adsorption material, a bridging agent for grafting the ionic liquids onto the substrate is a silane coupling agent; in which a preparation method is to acidly de-compose the silane coupling agent; carry out a grafting reaction with the substrate to connect the silane coupling agent onto the substrate; and then graft the ionic liquids onto the silane coupling agent under a neutral environment to form the ionic liquid impurity adsorption material in the solid state.

In certain embodiments, a recovery rate of the ionic liquid impurity adsorption material is not less than 95%.

In certain embodiments, in the purification operation, the aqueous phase liquid is heated to a liquid temperature between 85° C. and 150° C., so that the ionic liquid impurity adsorption material adsorbs the impurities under the liquid temperature.

In certain embodiments, after the separation operation, the method further includes implementing a crystallization operation, which includes cooling the aqueous phase liquid from the liquid temperature between 85° C. and 150° C. to a crystallization temperature between 5° C. and 25° C., so that the bis-2-hydroxylethyl terephthalate (BHET) crystallizes out of the aqueous phase liquid, thereby obtaining the recycled bis-2-hydroxylethyl terephthalate.

In certain embodiments, after the crystallization operation, the method further includes implementing a pelletizing operation to re-polymerize the recycled bis-2-hydroxylethyl terephthalate, and then to form recycled polyester pellets (r-PET).

In certain embodiments, the recycled bis-2-hydroxylethyl terephthalate has an "L" value not less than 85, an "a" value between −1.5 and 1.5, and a "b" value between −3.5 and 3.5; in which the recycled bis-2-hydroxylethyl terephthalate has the "L" value not less than 80, the "a" value between −3.0 and 3.0, and the "b" value between −7.0 after being tested for heat resistance at 180° C. during 1 hour.

Therefore, in the method for improving hue of recycled bis-2-hydroxylethyl terephthalate by using ionic liquids provided by the present disclosure, by virtue of "providing a recycled polyester fabric; using a chemical de-polymerization liquid to chemically de-polymerize the recycled polyester fabric to form a de-polymerization product; mixing the de-polymerization product with water to form an aqueous phase liquid; dispersing an ionic liquid impurity adsorption material into the aqueous phase liquid to adsorb impurities originally present in the recycled polyester fabric", the recycling quality and heat resistance of the bis-2-hydroxylethyl terephthalate (BHET) can be effectively improved. Furthermore, the method of the present disclosure has an advantage of involving a lower cost.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 1 is a schematic flow chart of a method for improving hue of recycled bis-2-hydroxylethyl terephthalate by using ionic liquids according to an embodiment of the present disclosure.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Method for Improving Hue of Recycled BHET by Using Ionic Liquids

Ordinary polyester fabrics usually have impurities such as dyes attached thereon. In order to recover polyester fabrics, a conventional recycling method essentially chemically de-polymerizes the polyester fabrics with a chemical de-polymerization liquid (i.e., ethylene glycol, EG) to form a de-polymerization product, and the de-polymerization product mainly includes bis-2-hydroxylethyl terephthalate (BHET).

Furthermore, in order to purify BHET, a conventional purification method is to use an activated carbon material or an ion exchange resin to absorb the impurities such as dyes from the crude BHET product containing ethylene glycol (EG), and then add water to crystallize the BHET. However, the hue, quality and heat resistance of BHET obtained by the conventional purification method are poor.

Another conventional purification method is to separate BHET by a three-stage distillation. Due to the need for three sets of thin film evaporators, this purification method will result in excessively high equipment costs, and since a BHET recovery rate of this purification method is not high, the conventional purification method has low economic benefits.

In order to solve the above-mentioned technical inadequacies, referring to FIG. 1, an embodiment of the present disclosure provides a method for improving hue of recycled bis-2-hydroxylethyl terephthalate by using ionic liquids. The method of the present embodiment can effectively improve a recycling quality of recycled bis-2-hydroxylethyl terephthalate and has an advantage of low cost.

Furthermore, the method of the present embodiment includes step S110, step S120, step S130, step S140, and step S150. It should be noted that the sequence of the steps and the actual operation way described in the present embodiment can be adjusted according to requirements, and are not limited to those described in the present embodiment.

The step S110 includes implementing a preparation operation. The preparation operation includes providing a recycled polyester fabric. The recycled polyester fabric is attached with impurities, and the impurities can be, for example, dyes and/or water repellents, but the present disclosure is not limited thereto.

For example, the recycled polyester fabric can be colored by dyes. Furthermore, the recycled polyester fabric can be treated with a water-repellent agent to have a water repellent function, for example. The dyes can be, for example, at least one of natural dyes and synthetic dyes. Alternatively, the dyes can be at least one of physical dyes and chemical dyes, for example. The water repellent can be, for example, silicon (Si) containing water repellent, fluorine (F) containing water repellent, fluorine and silicon containing water repellent, or water-based polyurethane (PU) water repellent, but the present disclosure is not limited thereto.

In an embodiment of the present disclosure, the recycled polyester fabric has an "L" value greater than 0 and not greater than 30 after dyeing. That is, the recycled polyester fabric has a darker color, but the present disclosure is not limited thereto. The aforementioned "L" value is a parameter value representing brightness in the Lab color space.

The step S120 includes implementing a de-polymerization operation. The de-polymerization operation includes using a chemical de-polymerization liquid to chemically de-polymerize the recycled polyester fabric to form a de-polymerization product. The de-polymerization product includes bis-2-hydroxylethyl terephthalate (BHET for short), oligomer, the chemical de-polymerization liquid, and the impurities.

More specifically, the chemical de-polymerization liquid can be, for example, ethylene glycol (EG). The method for chemically de-polymerizing the recycled polyester fabric can be, for example, an ethylene glycol de-polymerization method. Accordingly, the recycled polyester fabric can be de-polymerized into a de-polymerized product mainly including bis hydroxylethyl terephthalate (BHET). Furthermore, the de-polymerization product also includes oligomers formed by the de-polymerization of polyester fabrics, the above-mentioned chemical de-polymerization liquid (i.e., ethylene glycol) used for de-polymerization, and the impurities originally present in the recycled polyester fabric.

It is worth mentioning that the bis-2-hydroxylethyl terephthalate (BHET) is intermediates of pure terephthalic acid (PTA) and ethylene glycol (EG). Furthermore, the bis-2-hydroxylethyl terephthalate can also be used as a raw material for synthetic polyester (PET), and can also be used to form polyester copolymers with other monomers.

In an embodiment of the present disclosure, the chemical de-polymerization liquid chemically de-polymerizes the recycled polyester fabric in the presence of a de-polymerization catalyst. The de-polymerization catalyst can be, for example, a metal catalyst, but the present disclosure is not limited thereto. It is worth mentioning that the de-polymerization catalyst can assist in reducing the activation energy of the chemical de-polymerization liquid to chemically de-polymerize the polyester fabric.

In an embodiment of the present disclosure, the metal catalyst can be, for example, at least one material selected from a group consisting of zinc acetate, lead acetate, cadmium acetate, calcium acetate, or barium acetate, sodium acetate, lithium hydroxide, mercury acetate, copper acetate, and iron acetate. Alternatively, in an embodiment of the present disclosure, the metal catalyst can be, for example, an organic titanium metal catalyst. Alternatively, in an embodiment of the present disclosure, the metal catalyst can be, for example, an ionic liquid catalyst.

In an embodiment of the present disclosure, the chemical de-polymerization liquid is heated to a de-polymerization temperature to chemically de-polymerize the recycled polyester fabric. The de-polymerization temperature is preferably between 180° C. and 260° C., and more preferably between 210° C. and 240° C.

The step S130 includes implementing a purification operation to obtain purified bis-2-hydroxylethyl terephthalate (purified BHET) from the de-polymerized product.

The purification operation sequentially includes mixing the de-polymerization product with water to form an aqueous phase liquid; and then dispersing an ionic liquid impurity adsorption material in a solid state into the aqueous phase liquid, so that the ionic liquid impurity adsorption material adsorbs the impurities originally present in the recycled polyester fabric.

The aqueous phase liquid is heated to a liquid temperature between 85° C. and 150° C., so that the ionic liquid impurity adsorption material can adsorb the impurities under the liquid temperature, but the present disclosure is not limited thereto.

In an embodiment of the present disclosure, the ionic liquid impurity adsorption material can, for example, include: a substrate (i e, nano-magnetic material) and ionic liquids grafted onto the substrate. A preparation method of the ionic liquid impurity adsorption material includes acidifying a surface of the substrate made of carbon, silicon, iron, nickel, and/or cobalt, so that the surface of the substrate forms OH functional groups. Then, silane compounds are synthesized with the OH functional groups; and the ionic liquids are synthesized with the silane compounds. The ionic liquid impurity adsorption material can be used to adsorb impurities such as organic dyes.

In an embodiment of the present disclosure, the substrate is a granular material with a size of nanometer to micrometer, in which an average particle size of the substrate is preferably between 0.8 micrometers and 800 micrometers, and more preferably between 1 micrometer and 500 micrometers, but the present disclosure is not limited thereto.

In an embodiment of the present disclosure, a grafted quantity of the ionic liquids of the ionic liquid impurity adsorption material grafted onto per gram of the substrate is preferably between $10^6$ and $10^{20}$, and more preferably between $10^8$ and $10^{18}$, but the present disclosure is not limited thereto.

In an embodiment of the present disclosure, a weight ratio of the ionic liquid impurity adsorption material relative to the aqueous phase liquid is preferably in the range of 1:10-100. That is, the weight of the aqueous phase liquid is 10 to 100 times the weight of the ionic liquid impurity adsorption material, but the present disclosure is not limited thereto.

In an embodiment of the present disclosure, the ionic liquids of the ionic liquid impurity adsorption material are at least one material selected from a group consisting of 1-butyl-3-methylimidazolium hexafluorophosphate (BMI-PF6), 1-butyl-3-methylimidazolium tetrachlorozincate ($BMI_2ZnCl_4$), 1-butyl-3-methylimidazolium tetrachloroironate ($BMI_2FeCl_4$), 1-butyl-3-methylimidazolium tetrachloroironate ($BMI_2CoCl_4$), and 1-butyl-3-methylimidazolium tetrachlorocobaltate ($BMI-BF_4$), but the present disclosure is not limited thereto.

In an embodiment of the present disclosure, the substrate of the ionic liquid impurity adsorption material is made of at least one material selected from a group consisting of iron micro-particle, nickel micro-particle, carbon micro-particle, silicon micro-particle, and cobalt micro-particle.

The step S140 includes implementing a separation operation, which includes using a centrifugal method and/or a filtration method to collect the ionic liquid impurity adsorption material in a solid state that is dispersed in the aqueous phase liquid. More specifically, the separation operation includes using a centrifugal condition at 300 rpm to separate the ionic liquid impurity adsorption material, and/or using a 1 um filter device to collect the ionic liquid impurity adsorption material dispersed in the aqueous phase liquid.

Further, in the separation operation, the ionic liquid impurity adsorption material can be separated from the aqueous phase liquid by centrifugation, sedimentation, and filtration. A recovery rate of the ionic liquid impurity adsorption material is preferably not less than 95%, and more preferably not less than 99%.

In an embodiment of the present disclosure, the aqueous phase liquid and the ionic liquid impurity adsorption material are received in a container, and the ionic liquid impurity adsorption material is separated from the aqueous phase liquid by a 300 rpm rotating device, and then the ionic liquid impurity adsorption material is separated by a 1 um filter device, but the present disclosure is not limited thereto.

For example, in another embodiment of the present disclosure, the separation operation can also use high gravity fractionation to separate the ionic liquid impurity adsorption material that has adsorbed impurities from the aqueous phase liquid.

The step S150 includes implementing a crystallization operation. The crystallization operation includes cooling the aqueous phase liquid from the liquid temperature between 85° C. and 150° C. to a crystallization temperature between 5° C. and 25° C., so that the bis-2-hydroxylethyl terephthalate (BHET) crystallizes out of the aqueous phase liquid, thereby obtaining a recycled bis-2-hydroxylethyl terephthalate (recycled BHET).

In an embodiment of the present disclosure, the recycled bis-2-hydroxylethyl terephthalate has an "L" value not less than 85, an "a" value between −1.5 and 1.5, and a "b" value between −3.5 and 3.5. The recycled bis-2-hydroxylethyl terephthalate has the "L" value not less than 80, the "a" value between −3.0 and 3.0, and the "b" value between −7.0 and 7.0 after being tested for heat resistance at 180° C. during 1 hour.

The step S160 includes: implementing a granulation operation to re-polymerize the recycled bis-2-hydroxylethyl terephthalate, and then form recycled polyester pellets (r-PET). The recycled polyester pellets can be formed by pelletizing polymerized recycled bis-2-hydroxylethyl terephthalate using a single-screw pelletizer or a twin-screw pelletizer, for example.

Experimental Data and Test Results

In order to verify that the method for improving the hue of recycled bis-2-hydroxylethyl terephthalate by using ionic liquids provided by the examples of the present disclosure has a good recovery effect and a hue improvement effect, the following Exemplary Embodiments 1 to 3 will be compared with Comparative Examples 1 to 2 for illustrative purposes.

Exemplary Embodiment 1

Exemplary Embodiment 1 uses a solid ionic liquid, synthesized with activated carbon (average particle size 57.4 μm, particle size range 4-275 μm), chloro-propyl-trimethoxy-silica and 1-butyl-3-methyl-imidazole hexa-fluoro-phosphate, as a de-polymerization catalyst and color removal carrier (SDC-1).

Exemplary Embodiment 1 takes 1 kg of polyester fabric (PET fabric) and 6 kg of ethylene glycol (EG) into a 10 L of three-necked glass bottle to form a de-polymerization liquid. The de-polymerization liquid was heated to 190° C., stirred and reacted for 4 hours, and then cooled to 120° C. and stirred for 1 hour to form a de-polymerized product, which includes BHET. 7 kg of water was mixed with the de-polymerization product to form an aqueous phase liquid, and the solid ionic liquid (SDC-1) was added into the aqueous phase liquid to enable the solid ionic liquid (SDC-1) to adsorb the impurities, such as dyes, originally present in the PET fabric. The solid ionic liquid (SDC-1) was separated from the aqueous phase liquid by centrifugation at 300 rpm. The solid ionic liquid (SDC-1) was filtered with a 1 um filter device. EG and other substances were distilled out of the aqueous phase liquid under the conditions of a pressure of 5 torr and a temperature of 150° C. The temperature of the aqueous phase liquid was then lowered to 90° C. to dissolve BHET in water. The 90° C. BHET-containing aqueous solution was cooled to 50° C. with cooling water to precipitate BHET crystals (first stage of cooling and crystallization), where a cooling rate was 8° C./min, and the solid BHET was removed by filtration. The liquid mother liquor underwent a second stage of cooling and crystallization.

The 50° C. BHET-containing aqueous solution was cooled to 5° C. with chilled water to precipitate BHET crystals, where a cooling rate was 0.2° C./min, and the solid BHET was removed by filtration.

After mixing and drying the solid BHET crystallized in the first stage and the second stage of cooling and crystallization, the resulting BHET quality was L=90, a=0.4, b=1.5. The solid BHET was put in an oven for 1 hour at 180° C., and the resulting BHET quality was L=86, a=0.7, and b=5.6. A recovery rate of the solid ionic liquid was 98.4%.

Exemplary Embodiment 2

Exemplary Embodiment 2 was approximately the same as Exemplary Embodiment 1, except that Exemplary Embodiment 2 used a solid ionic liquid, synthesized with silicon (average particle size 65.3 um, particle size range 3-270 um), chloro-propyl-trimethoxy-silica, and 1-butyl-3-methyl-imidazole hexa-fluoro-phosphate, as a de-polymerization catalyst and color removal carrier (SDC-2). The remaining conditions of Exemplary Embodiment 2 were the same as those of Exemplary Embodiment 1.

The resulting solid BHET quality of Exemplary Embodiment 2 was L=89, a=0.6, and b=2.5. The solid BHET of Exemplary Embodiment 2 was put in an oven at 180° C., and maintained for 1 hour. The solid BHET quality after heating was L=84, a=1.1, and b=6.3. The recovery rate of the solid ionic liquid was 98.8%.

Exemplary Embodiment 3

Exemplary Embodiment 3 was approximately the same as Exemplary Embodiment 1, except that Exemplary Embodiment 3 used a solid ionic liquid, synthesized with metallic nickel (average particle size 71.0 um, particle size range 8-300 um), chloro-propyl-trimethoxy-silica, and 1-butyl-3-methyl-imidazole hexa-fluoro-phosphate, as a de-polymerization catalyst and color removal carrier (SDC-3). The remaining conditions of Exemplary Embodiment 3 were the same as those of Exemplary Embodiment 1.

The resulting solid BHET quality of Exemplary Embodiment 3 was L=92, a=0.1, and b=1.1. The solid BHET of Exemplary Embodiment 3 was put in an oven at 180° C., and maintained for 1 hour. The solid BHET quality after heating was L=85, a=0.9, and b=5.9. The recovery rate of the solid ionic liquid was 99.3%.

Comparative Example 1

In Comparative Example 1, 1 kg of polyester fabric (PET fabric), 6 kg of ethylene glycol (EG) and 20 g of zinc acetate catalyst were put into a 10 L three-necked glass bottle to form a reaction liquid. The temperature of the reaction liquid was raised to 190° C., and the reaction liquid was stirred for 6 hours.

The reaction liquid was distilled out of EG and other substances at a pressure of 5 torr and a temperature of 150° C. After the reaction liquid was cooled to 90° C., 7 kg of water was added to the reaction liquid to form an aqueous phase liquid, and the temperature of the aqueous phase liquid was maintained at 90° C. to dissolve BHET in water. Then, 30 g of activated carbon was added to the aqueous phase liquid, the aqueous phase liquid was maintained at 90° C. and stirred for 1 hour, so that the activated carbon could adsorb dyes and other impurities, and the activated carbon was removed by filtration.

The 90° C. BHET-containing aqueous solution was cooled to 50° C. with cooling water to crystallize BHET, where a cooling rate was 8° C./min, and the solid BHET was removed by filtration. The liquid mother liquor underwent a second stage of cooling and crystallization.

The 50° C. BHET-containing aqueous solution was cooled to 5° C. with chilled water to precipitate BHET crystals, where a cooling rate was 0.2° C./min, and the solid BHET was removed by filtration.

After mixing and drying the solid BHET crystallized in the first stage and the second stage of cooling and crystallization, the BHET quality was that L=84%, a=2.2, b=4.4. The solid BHET of Comparative Example 1 was kept in an oven at 180° C. for 1 hour, the BHET quality after heated was that L=76, a=3.4, and b=20. The recovery rate of the catalyst was 0% since the catalyst was not easy to recycle when dissolved in water.

Comparative Example 2

Comparative Example 2 was approximately the same as Comparative Example 1, except that Comparative Example 2 used 50 g of activated carbon instead of 30 g of activated carbon for color removal. The remaining process conditions of Comparative Example 2 were the same as those of Comparative Example 1.

The BHET quality of Comparative Example 2 was that L=90%, a=0.8, and b=3.1. The BHET of Comparative Example 2 was kept in an oven at 180° C. for 1 hour, and the BHET quality after heated was that L=77, a=2.7, and b=15. The recovery rate of the catalyst was 0% since the catalyst was not easy to recycle when dissolved in water.

Beneficial Effects of the Embodiments

In conclusion, in the method for improving hue of recycled bis hydroxylethyl terephthalate by using ionic liquids provided by the present disclosure, by virtue of "providing a recycled polyester fabric; using a chemical de-polymerization liquid to chemically de-polymerize the recycled polyester fabric to form a de-polymerization product; mixing the de-polymerization product with water to form an aqueous phase liquid; dispersing an ionic liquid impurity adsorption material into the aqueous phase liquid to adsorb impurities originally present in the recycled polyester fabric", the recycling quality and heat resistance of the bis-2-hydroxylethyl terephthalate (BHET) can be effectively improved. Furthermore, the method of the present disclosure has an advantage of involving a lower cost.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for improving hue of recycled bis-2-hydroxylethyl terephthalate by using ionic liquids, comprising:
    implementing a preparation operation, which includes providing a recycled polyester fabric, the recycled polyester fabric containing impurities;
    implementing a de-polymerization operation, which includes using a chemical de-polymerization liquid to chemically de-polymerize the recycled polyester fabric to form a de-polymerization product, the de-polymerization product including the bis-2-hydroxylethyl terephthalate (BHET) and the impurities;
    implementing a purification operation, which includes mixing the de-polymerization product with water to form an aqueous phase liquid; and then dispersing an ionic liquid impurity adsorption material in a solid state into the aqueous phase liquid, so that the ionic liquid impurity adsorption material adsorbs the impurities originally present in the recycled polyester fabric,
        wherein the ionic liquid impurity adsorption material includes a substrate and the ionic liquids grafted onto the substrate, the substrate is a granular material and has an average particle size of between 57.4 micrometers and 71.0 micrometers,
        wherein, in the ionic liquid impurity adsorption material, a grafted quantity of the ionic liquids grafted onto per gram of the substrate is between $10^6$ and $10^{20}$,
        wherein, in the purification operation, a weight ratio of the ionic liquid impurity adsorption material relative to the aqueous phase liquid is in the range of 1:10-100, the aqueous phase liquid is heated to a liquid temperature of between 85° C. and 150° C., and the ionic liquid impurity adsorption material adsorbs the impurities under the liquid temperature; and
    implementing a separation operation, which includes using a centrifugal method and/or a filtering method to collect the ionic liquid impurity adsorption material in the solid state that are dispersed in the aqueous phase liquid.

2. The method according to claim 1, wherein, in the de-polymerization operation, the chemical de-polymerization liquid is ethylene glycol (EG), and the chemical de-polymerization liquid is heated to a de-polymerization temperature that is between 180° C. and 260° C. to chemically de-polymerize the recycled polyester fabric.

3. The method according to claim 1, wherein, in the ionic liquid impurity adsorption material, the ionic liquids are at least one material selected from a group consisting of 1-butyl-3-methylimidazolium hexafluorophosphate (BMI-PF6), 1-butyl-3-methylimidazolium tetrachlorozincate ($BMI_2ZnCl_4$), 1-butyl-3-methylimidazolium tetrachloroironate ($BMI_2FeCl_4$), 1-butyl-3-methylimidazolium tetrachloroironate ($BMI_2CoCl_4$), and 1-butyl-3-methylimidazolium tetrachlorocobaltate ($BMI-BF_4$).

4. The method according to claim 1, wherein, in the ionic liquid impurity adsorption material, a bridging agent for grafting the ionic liquids onto the substrate is a silane coupling agent; wherein a preparation method of the ionic liquid impurity adsorption material is to acidly de-compose the silane coupling agent; carry out a grafting reaction with the substrate to connect the silane coupling agent onto the substrate; and then graft the ionic liquids onto the silane coupling agent under a alkaline aqueous environment to form the ionic liquid impurity adsorption material in the solid state.

5. The method according to claim 1, wherein a recovery rate of the ionic liquid impurity adsorption material is not less than 95%.

6. The method according to claim 1, wherein, after the separation operation, the method further includes implementing a crystallization operation, which includes cooling the aqueous phase liquid from the liquid temperature between 85° C. and 150° C. to a crystallization temperature that is between 5° C. and 25° C., so that the bis-2-hydroxylethyl terephthalate (BHET) crystallizes out of the aqueous phase liquid, so as to obtain the recycled bis-2-hydroxylethyl terephthalate.

7. The method according to claim 6, wherein, after the crystallization operation, the method further includes implementing a pelletizing operation to re-polymerize the recycled bis-2-hydroxylethyl terephthalate, and then to form recycled polyester pellets (r-PET).

8. The method according to claim 7, wherein the recycled bis-2-hydroxylethyl terephthalate has an "L" value not less than 85, an "a" value between-1.5 and 1.5, and a "b" value between −3.5 and 3.5; wherein after the recycled bis-2-hydroxylethyl terephthalate undergoes a heat resistance test for 1 hour, the recycled bis-2-hydroxylethyl terephthalate has the "L" value not less than 80, the "a" value between-3.0 and 3.0, and the "b" value between −7.0 and 7.0.

9. The method according to claim 1, wherein, in the purification operation, the substrate of the ionic liquid impurity adsorption material is made of at least one material selected from a group consisting of carbon micro-particle and silicon micro-particle, and the average particle size of the substrate is between 57.4 micrometers and 65.3 micrometers.

\* \* \* \* \*